United States Patent [19]

Morita et al.

[11] Patent Number: 5,300,525
[45] Date of Patent: Apr. 5, 1994

[54] ANTI-SOLID TUMOR AGENTS

[75] Inventors: Yoshiharu Morita, Yokohama; Koichiro Hirayama, Sagamihara, both of Japan

[73] Assignee: Mitsubishi Kasei Corporation, Tokyo, Japan

[21] Appl. No.: 841,785

[22] Filed: Mar. 2, 1992

Related U.S. Application Data

[60] Continuation of Ser. No. 688,694, Apr. 22, 1991, abandoned, which is a continuation of Ser. No. 461,671, Jan. 8, 1990, abandoned, which is a division of Ser. No. 72,141, Jul. 10, 1987, Pat. No. 4,916,160.

Foreign Application Priority Data

Jul. 10, 1986 [DL] 07101986 ................ 162783

[51] Int. Cl.$^5$ ............................................. A61K 31/225
[52] U.S. Cl. ................................................. 514/548
[58] Field of Search ......................................... 514/548

[56] References Cited

FOREIGN PATENT DOCUMENTS 56-61317 5/1981 Japan .
56-61318 5/1981 Japan .
56-61372 5/1981 Japan .

OTHER PUBLICATIONS

*Tetrahedron Letters*, vol. 30, No. 10, 1989, pp. 1173–1176.
*Patent Abstracts of Japan*, vol. 5, No. 124 (C-66) [796], 1981.
*Tetrahedron Letters*, vol 24, No. 22, 1983, pp. 2267–2270.
*Carcinogenesis*, vol 6, No. 8, 1985, pp. 1189–1194.
*Lloydia*, vol. 38, No. 5, 1975, pp. 378–382.
*Patent Abstracts of Japan*, vol. 5, No. 124 (C-66) [796], 1986.
*Patent Abstracts of Japan*, vol. 5, No. 62 (C-52) [734], 1981.
*The Merck Manual*, 14th ed., 1982 pp. 2378–2383.
*Chemical Reviews*, 1988, vol. 88, No. 5, pp. 719–732.
*Tetrahedron*, vol. 41, No. 6, pp. 1049–1056 (1985), D. Czarkie, et al., "Attempted Acid-Catalyzed Transannular Reactions in the Cembranoids".
*Chemical Pharm. Bull.*, vol. 29, (1), pp. 82–87 (1981), Nakagawa et al.
*Chemical Pharm Bull.*, vol.27 (10), pp. 2382–2387 (1979), Kobayashi, et al.
*The Merck Manual*, 14th ed., 1982, pp. 1137–1146, 2375–2377.
*Eur. J. Cancer*, 1980, 16(9), pp. 1133–1140.

*Primary Examiner*—Jerome D. Goldberg
*Attorney, Agent, or Firm*—Oblon, Spivak, McClelland, Maier & Neustadt

[57] ABSTRACT

According to the present invention, there is provided an anti-solid tumor agent comprising a cembrane-type compound represented by the general formula (I) or (II):

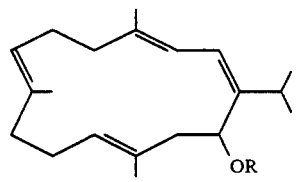

(I)

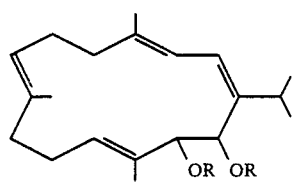

(II)

wherein R is a hydrogen atom or an acyl group, as an effective ingredient.

6 Claims, 3 Drawing Sheets

ANTI-SOLID TUMOR AGENTS

This application is a continuation of application Ser. No. 07/688,694, filed on Apr. 22, 1991, which was a continuation of U.S. Ser. No. 07/461,671 filed Jan. 8, 1990, now both abandoned, which is a division of application Ser. No. 07/072,141, filed on Jul. 10, 1987, now U.S. Pat. No. 4,916,160.

BACKGROUND OF THE INVENTION

1. Field of the Invention

The present invention relates to a method of treating solid tumors in a mammal using pharmaceutical compositions described hereinbelow, the solid tumors treated being those which are sensitive to treatment with the compositions.

2. Description of the Prior Art

Many recent studies have been showing that various external and internal environmental substances may cause carcinogenesis.

By way of illustration, in the so-called two-stage model of carcinogenesis of mouse skin cancer, which has been well known as a representative of mouse cancers, the carcinogenic process may be described as follows: in the first stage, upon administration of a small amount of dimethylbenzanthracene (DMBA) insufficient to cause carcinogenesis, normal cells are converted into latent tumoral ones which are in an initiated state, this stage being referred to as carcinogenic initiation; and, in the second stage, the latent cancerous cells in the initiated state are altered from benign tumor to malignant tumor by the action of a substance capable of promoting the carcinogenesis, for example, 12-O-tetradecanoylphorbol 13-acetate (TPA); thus, carcinogenesis is performed.

Recently, both studies on causative substances promoting carcinogenesis by such carcinogenic processes and biochemical studies on carcinogenic processes have notably been advanced. These studies can be applied to inhibition of carcinogenesis, and inhibition and/or prophylactic prevention of progression and growth of cancer. Refer to, for instance, "Cellular Interactions by Environmental Tumor Promoters", edited by Hirota Fujiki et al., Japan Scientific Societies Press (1984).

Such two-stage carcinogenesis has been reported on mouse breast cancer promoted by mouse epidermal growth factor (EGF): Takami Oka, Nippon Yaku-gakkai (Japan Pharmacy Association), the 106th annual meeting, collection of summaries of lectures, page 283 (1986). Such processes may also be observed in rats. In addition, it has also been reported that rat solid cancers found in organs other than skin, for example, liver, bladder, large intestine, stomach or duodenum, will be produced by the two-stage processes.

Further, epidemiologic data have shown that such a solid tumor as human lung, large intestine, esophagus, nasopharynx or uterus cancer is produced by multistage cancinogenesis: Hiroshi Yamazaki, Taisha (Metabolism), Vol. 17, Extra Edition, "Gan (Cancer) '80", pp. 21-32 (1980). The known tumor promoters (promoters of carcinogenesis) of these cancers are, respectively, smoking, bile acid, phorbol ester, nickel, and coupled estrogen.

In addition, changes in incidences of cancer by settlement may be considered to depend on respective environmental factors: for instance, in Japanese Isseis who have emigrated to the United States, the incidence of large intestine cancer increases and the mortality from prostata cancer differs. These differences suggest that human cancers are formed by multi-stage carcinogenesis.

It has been known that among various biochemical reactions caused by carcinogenesis-promoting substances, ornithine decarboxylase (ODC) activity increases temporarily: Masami Suganuma, Toxicology Forum, Vol. 7, No. 6, page 616 (1984). Researches after other tumor promoting substances using such ODC activity as an index have led to discovery of new many tumor promoters.

Consequently, it has been proved that like TPA, teleocidin and aplysiatoxin are also potent tumor promoters of mouse skin cancer: Hirota Fujiki, Taisha (Metabolism), Vol. 18, Extra Edition, "Gan (Cancer) '81" (1981); and ibid., Vol. 22, "Gan (Cancer) '81" (1985).

Anti-tumor promoters (Anti-promoters of carcinogenesis) capable of inhibiting such two-stage carcinogenesis as aforementioned may be promising as substances for inhibiting the carcinogenic processes for the purpose of prophylactic inhibition of canceration, prevention of malignant alteration, prophylactic prevention of recurrence and cure of cancer. Many substances have been known as such anti-tumor promoters.

Among retinoids, for example, many low toxic substances have been searched, and it has been known that anti-carcinogenesis promoters represented by 13-cis-retinoic acid may prophylactically prevent carcinogenesis at the same level of activity as the tumor promoters.

On the other hand, it is also possible that anti-carcinogenic promoters present as living environmental factors, such as quercetine, which is one of flavonoids, tannin contained in tea, and pentagalloylglucose, may prophylactically prevent carcinogenesis. Probably, lower toxic substances having such anti-carcinogenic promoter activity will be utilized as new cancer-inhibiting agents in the future from the viewpoint of the prevention and/or inhibition of carcinogenesis.

SUMMARY OF THE INVENTION

Under the aforementioned circumstances, the present inventors have made great efforts to find low toxic substances having the anti-tumor promoter activity, and finally found that specific cembrane-type diterpene compounds, which have been known to have the anti-leukemic activity, may have potent anti-tumor promoter activity, and that such compounds are particularly effective in promoting the conversion of latent cancer cells, which are those derived from normal cells by initiating primarily with external factors, into benign solid tumor and also effective in prophylactically preventing and inhibiting the progression of such latent cancer cells into malignant solid tumor. Thus, the present invention has been attained.

According to the invention, there are provided anti-solid tumor agents containing, as effective ingredients, cembrane-type diterpene compounds represented by the following general formula (I) or (II):

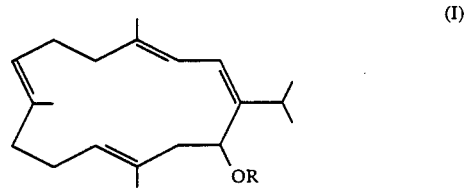

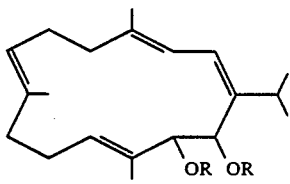
(II)

wherein R is a hydrogen atom or an group.

BRIEF DESCRIPTION OF THE DRAWINGS

In the attached drawings.

DESCRIPTION OF THE INVENTION

Figure 1:
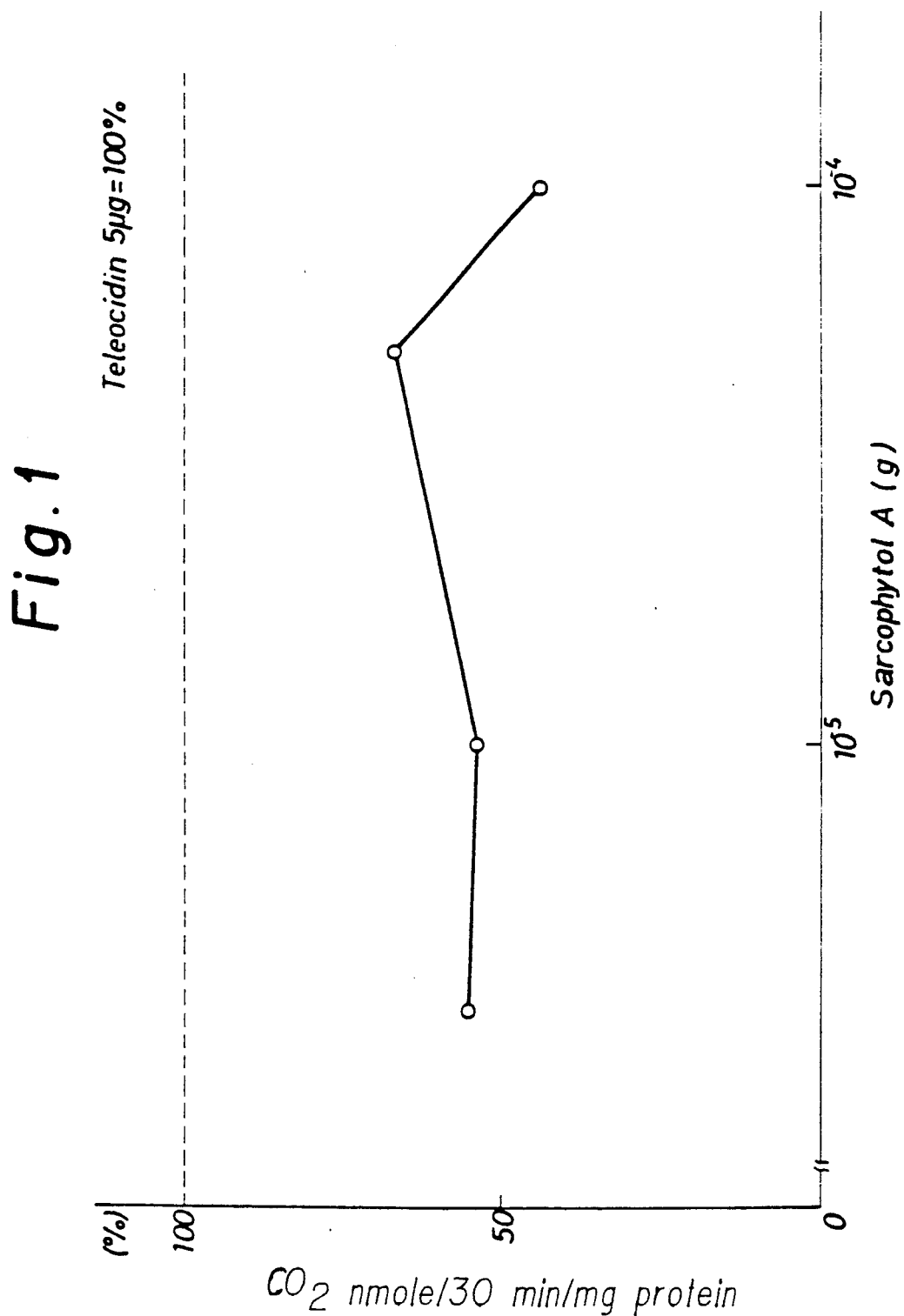
FIGS. 1-3 show, respectively, the inhibiting effect on the ODC activity-induction, the inhibiting effect on the mouse skin two-stage carcinogenesis, and the change of mouse body weight upon administration, of the anti-solid tumor agents according to the invention.

The invention will hereinbelow be described in detail.

The cembrane-type diterpene compounds used in the invention are represented by the general formula (I) or (II) shown above.

In these formulae, R represents a hydrogen atom or an acyl group. Preferably, the acyl groups include acetyl, propionyl, butyryl and benzoyl groups.

These cembrane-type diterpene compounds may be prepared by known methods described in e.g. Japanese Patent Application Laying-open (KOKAI) Nos. 61317/81 and 61318/81. In the processes disclosed therein, the cembrane type diterpene compounds may be separated from a lipid fraction of an extract from the soft coral, Sarcophyton glaucum, Ohumikinoko by silica gel column chromatography.

Ohumikinoko generally lives on coral reefs in the Indian Ocean and the Pacific Ocean. For example, it has been known that Ohumikinoko living in the Red Sea contains sarcophine and 16-deoxosarcophine: J. Bernstein et al., Tetrahedron, 30, 2817 (1974) United Kingdom; and Y. Kashman et al., Tetrahedron, 30, 3615 (1974) United Kingdom.

Substances contained in Ohumikinoko extracts may vary depending on the time and place at which samples of Ohumikinoko are collected. Accordingly, the time and place should be suitably chosen.

Before extraction, it is preferred that samples of Ohumikinoko are dried and sliced into small pieces so as to eliminate the viscosity of their surface.

Solvents for the extraction may include organic solvents, for example, alcohols such as methanol, ethanol and isopropanol, halogenated hydrocarbons such as chloroform, hydrocarbons such as benzene, hexane and heptane, ethers such as ethyl ether, isopropyl ether and dioxane, ketones such as acetone and methyl ethyl ketone, esters such as ethyl acetate, and mixtures of any of the foregoing.

To avoid oxidative degradation of the active substances contained in the extract, the extracting operation is preferably carried out either under conditions where the area to be contacted with air should be as small as possible, or under inert gas atmosphere.

The extraction may be carried out at room temperatures, but preferably is may be performed while heating so as to accelerate the extraction speed.

The liquid extract obtained by separation from residues in any conventional manner may be subjected to the usual distillation procedures to remove the solvent. Thus, a crude extract is obtained.

The crude extract may be subjected to fractionation by any usual method, e.g., one described by J. Folch et al. in J. Biol. Chem., 226, 497 (1957) USA, to obtain a lipid fraction.

The thus obtained lipid fraction of the extract from Ohumikinoko is a viscous, brown oil.

Such a fraction may be further purified by chromatography, such as column or preparative thin layer chromatography.

Solid materials packed in columns for chromatography may include silica gel, alumina, cellulose powder, active carbon, etc. Eluents may be suitably chosen depending on the packed materials. When silica gel is used, chloroform, hexane/benzene (volume ratio=-about 3:1 to 1:1), or hexane/ethyl acetate (volume ratio=0.9-0.95:0.1-0.05) is preferably employed.

The fraction thus obtained may be still further purified and/or isolated by column chromatography using different packing materials and eluent solvents.

Gels used for preparative thin layer chromatography may include silica gel, alumina, cellulose powder, etc. Developing solvents may preferably be chloroform or a mixed chloroform-ether solvent.

Among compounds thus obtained, one represented by the general formula (I) in which R is a hydrogen atom has been called sarcophytol-A.

This sarcophytol-A may be acylated in a conventional manner to give an acylated product such as sarcophytol-A acetate. The acylated ester of sarcophytol-A may be hydrolyzed by conventional methods to obtain again sarcophytol-A.

On the other hand, the compound obtained in a similar manner and represented by the general formula (II) in which R is a hydrogen atom has been called sarcophytol-B.

The sarcophytol-B may also be acylated in a conventional manner to give an acylated product such as sarcophytol-B diacetate. The acylated ester of sarcophytol-B may in turn be hydrolyzed in a conventional method to obtain sarcophytol-B.

The anti-solid tumor agents according to the present invention contain the above described cembrane-type diterpene compounds as effective ingredients.

In accordance with the present invention, the solid tumors treated are those which are sensitive to treatment with the compounds and compositions of the present invention.

Solid tumors to which the agents of the present invention are to be effectively applied may include benign and malignant tumors of massive organs, such as gullet, oral cavity, stomach, duodenum, small intestine, large intestine, anus, gallbladder, labium, nasopharynx, liver, skin, pancreas, bronchus, lung, mammary gland, uterus, ovary, prostate gland, male genital organ and urinary organs (bladder, kidney).

The ornithine decarboxylase (ODC) activity of the aforementioned tumor promoters such as TPA and teleocidin will cause a temporary, strong induction in the mouse skin after 4-5 hours. The cembrane-type diterpene compounds according to the present invention, e.g., sarcophytol-A, may inhibit such induction by the ODC activity with their activity levels being equivalent with the tumor promoters.

Further, even in the two stage model of carcinogenesis of mouse skin cancer, the cembrane-type diterpene compounds, e.g., sarcophytol-A, according to the present invention greatly retarded and inhibited the carcinogenesis of mouse skin cancer at the same concentration (5.6 nmole) as the tumor promoter teleocidin.

That is to say, the anti-solid tumor agents of the invnention will prevent the recurrence of cancers, or will prevent the carcinogenesis when the possibility of carcinogenesis is high, or will inhibit the progression of the cancer when already cancerated.

In the present invention, the compound represented by the general formula (I) or II may be administered solely or in combination with a pharmaceutically acceptable carrier or vehicle. Its composition will be determined according to the administration route and plan.

Dose amounts will depend on ages, body weights, degrees of symptoms, etc. of patients. If the drugs are administered orally, large amounts should be used in order to obtain results equivalent to those attained in parenteral administration.

The dose amounts effective for prophylactically preventing and/or inhibiting solid tumors will generally range from 50 micrograms to 1,000 milligrams per kilogram of body weight a day in parenteral administration, and from 100 micrograms to 2,000 milligrams per kilogram of body weight a day.

Parenteral adminisrtation will be done in sterilized solutions or suspensions. Rectal and oral administration may be done in the form of tablets, capsules, powders, granules, solutions or elixirs. Such dosage forms of drugs may contain one or more pharmaceutically acceptable, non-toxic, solid or liquid carriers or vehicles in addition to at least one active ingredient.

Examples of solid carriers may include conventional gelatine capsules. One or more active ingredients with or without one or more adjuvants can be tabletted, granulated or pulverized, and they can then be packaged. Vehicles which may be used together with the active compounds of the invention include water; gelatine; sugars such as lactose and glucose; starchs such as corn, wheat, rice and arrowroot starch; fatty acids such as stearic acid; fatty acid salts such as calcium stearate and magnesium stearate; talc; vegetable oil; alcohols such as stearyl alcohol and benzyl alcohol; gum; polyalkylene glycols; and the like.

These capsules, tablets, granules and powders may generally contain 5 to 100% by weight, preferably 25 to 100% by weight, of the effective ingredient(s).

Liquid carriers may include water and animal- or plant-derived or synthetic oils such as petroleum, soybean oil, peanut oil, sesame oil, mineral oil, and the like. Usually, preferred liquid carriers are saline, sugars such as dextrose, glycols such as ethylene glycol, propylene glycol and polyethylene glycol.

when the drugs are administered parenterally, i.e., by intramuscular, intravenous or subcutaneous injections, sterilized solutions to which sodium chloride or other solute such as glucose is added so as to make the solutions isotonic may be employed.

Solvents suitable for use in injections may include sterilized water, lidocaine hydrochloride (for intramuscular injections), saline, glucose, liquids suitable for intravenous injections, electrolyte solutions (for intravenous injections), and the like. These injections may usually contain 0.5 to 20% by weight, preferably 1 to 10% by weight, of the effective ingredient(s).

Liquid drugs for oral administration may preferably be suspensions or syrups containing 0.5 to 10% by weight of the effective ingredient(s). The carriers contained in such liquid drugs may be water-like vehicles such as perfumes, syrups, pharmaceutical micelles, and the like.

Further, the drugs can also be applied in the form of external ointments, creams, or lotions.

The anti-solid tumor agents according to the present invention will act as anti-tumor promoters, and may prophylactically prevent solid tumors and even inhibit the progression and/or propagation of cancerated solid tumors. Thus, the agents are effective in prophylactically preventing and/or inhibiting solid tumors.

DESCRIPTION OF THE PREFERRED EMBODIMENTS

The invention will be further illustrated by the following non-limiting examples. These examples are given by way of illustration only and they should not be construed as limiting the scope of the present invention defined in the attached claims.

EXAMPLES 1, 2 AND 3

Inhibiting effect on ODC activity induction (I)

The test for measuring the ODC activity was performed according to the method described by Masami Suganuma in Toxicology Forum, 7, 616 (1984). A crude enzyme solution extracted from mouse skin on which a tumor promoter teleocidin had applied was used as a control. It was observed that in mice treated with a mixture of 5 micrograms (11.4 nmole) of teleocidin and 3.28 micrograms (11.4 nmole) of sarcophytol A, the ODC activity was substantially inhibited as compared with the control.

Sarcophytol A acetate and sarcophytol B were also tested in a like manner. Similarly, the ODC activity was inhibited.

These results are shown in Table below.

TABLE

| | Compound | Dose amount | Inhibition rate (%) |
|---|---|---|---|
| Example 1 | Sarcophytol A* | 1 mg | 55.4 |
| | | 3.28 μg | 65.2 |
| Example 2 | Sarcophytol A acetate* | 1 mg | 48.3 |
| | | 3.76 μg | 0 |
| Example 3 | Sarcophytol B** | 1 mg | 31.7 |
| | | 3.45 μg | 19.6 |

Control = Teleocidin 5 micrograms (11.4 nmole)
*Prepared by the method described in Japanese Patent Application (KOKAI) No. 61318/81 (Examples 1 and 2)
**Prepared by the method described in Japanese Patent Application (KOKAI) No. 61317/81 (Example 1).

EXAMPLE 4

Inhibiting effect on ODC activity induction (II)

ODC activities in CD-1 mice to which 0.033 to 1 microgram of sarcophytol A was intraperitoneally injected were compared with the control crude enzyme solutions extracted from CD-1 mouse skin on which 5 micrograms of teleocidin as a tumor promoter had been applied. The results (% inhibition rate) are shown in FIG. 1.

As seen from FIG. 1, sarcophytol A was taken up and inhibited the ODC activity.

EXAMPLES 5 AND 6 AND COMPARATIVE EXAMPLE 1

Inhibiting effect on mouse skin two-stage carcinogenesis

Figure 2:
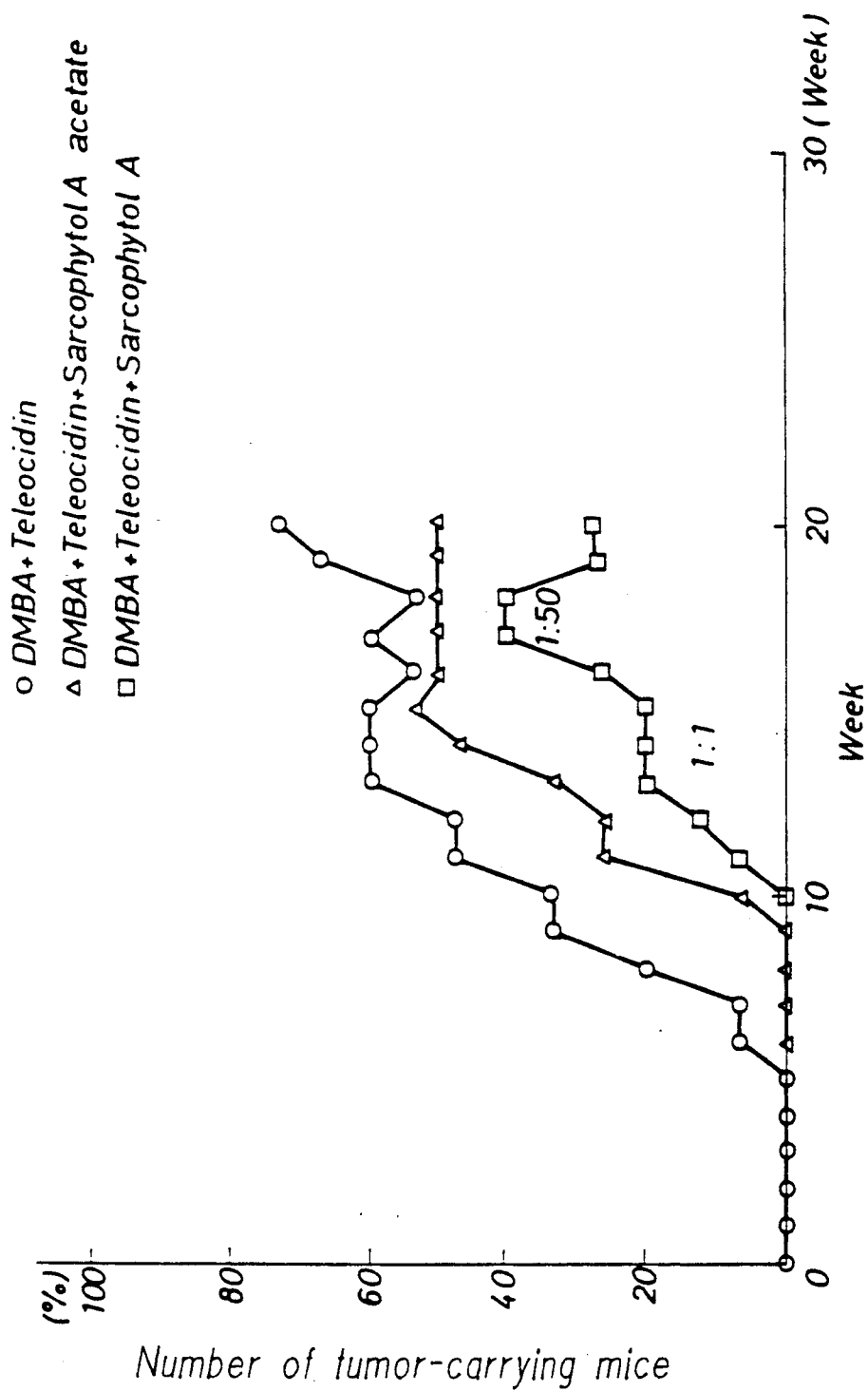

For comparison purpose, 100 micrograms of dimethylbenzanthracene (DMBA) was administered to female CD-1 mice of 8 week old to initiate and 2.5 micrograms (5.6 nmole) of teleocidin as a tumor promoter was then applied on the mice skin twice a week (Comparative Example 1). In Examples 5 and 6, respectively, either 1.6 micrograms (5.6 nmole) of sarcophytol A or 1.8 micrograms (5.6 nmole) of sarcophytol A acetate was applied on the mice skin, 15 minutes before the application of teleocidin. In Example 5, the ratio of teleocidin to sarcophytol A was changed to 1:50 in the 17th week. The results are illustrated in FIG. 2.

EXAMPLE 7

Figure 3:
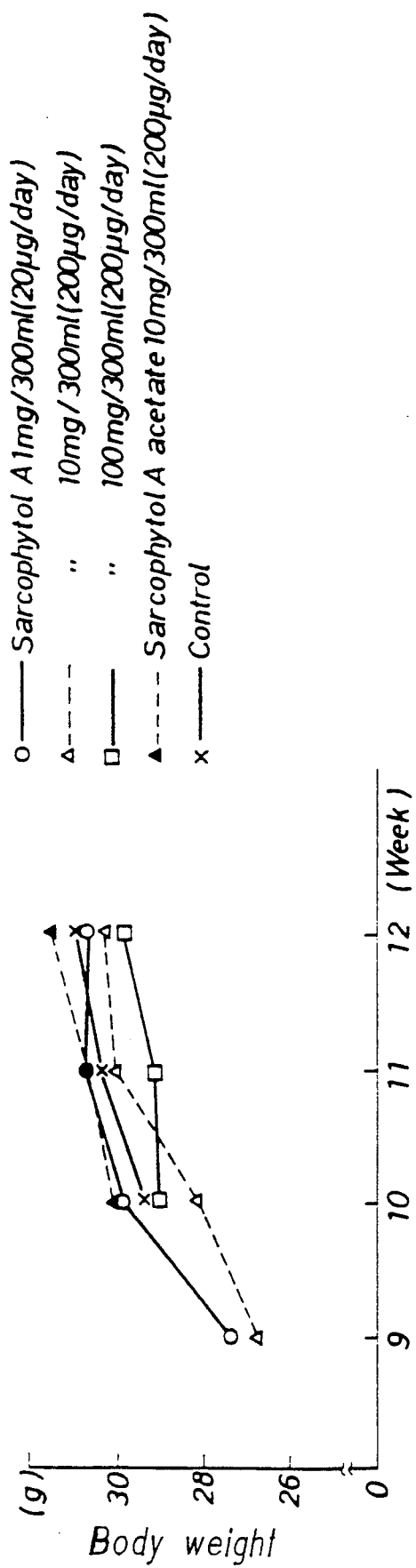

Change of body weight upon administration of sarcophytol A or sarcophytol A acetate To female CD-1 mice of 8 week old, water containing sarcophytol A (1 mg/300 ml, 10 mg/300 ml or 100 mg/300 ml) or sarcophytol A acetate (10 mg/300 ml) was given in an amount of 6 ml a day. The change of body weights of the mice was observed. The results are illustrated in FIG. 3.

What is claimed is:

1. A method of treating solid tumors in a mammal, which comprises administering to said mammal an effective amount of a pharmaceutical composition, which comprises:

a) an effective amount for treating solid tumors of a compound of the formula:

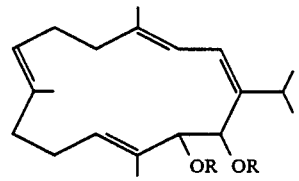

wherein R is selected from the group consisting of butyryl and benzoyl, and b) a pharmaceutically acceptable carrier, and wherein said solid tumors treated are sensitive to treatment with said composition containing said compound.

2. The method of claim 1, wherein R is butyryl.
3. The method of claim 1, wherein R is benzoyl.
4. The method of claim 1, wherein said mammal is a human.
5. The method of claim 1, wherein said solid tumors are selected from the group consisting of tumors of the gullet, oral cavity, stomach, duodenum, small intestine, large intestine, anus, gall bladder, labium, nasopharynx, liver, skin, pancreas, bronchus, lung, mammary gland, uterus, ovary, prostate gland, male genital organ and urinary organs.
6. The method of claim 5, wherein said urinary organs are selected from the group consisting of the bladder and the kidney.

* * * * *

UNITED STATES PATENT AND TRADEMARK OFFICE
CERTIFICATE OF CORRECTION

PATENT NO. : 5,300,525
DATED : April 5, 1994
INVENTOR(S) : Yoshiharu MORITA, et al.

It is certified that error appears in the above-indentified patent and that said Letters Patent is hereby corrected as shown below:

On the title page, Item [30], the Foreign Application Priority Data should read as follows:

--Jul. 10, 1986 [JP]  Japan ................. 61-162783--

Signed and Sealed this

Ninth Day of August, 1994

Attest:

BRUCE LEHMAN

*Attesting Officer*     Commissioner of Patents and Trademarks